United States Patent [19]

Sublette

[11] Patent Number: 4,880,542
[45] Date of Patent: Nov. 14, 1989

[54] BIOFILTER FOR THE TREATMENT OF SOUR WATER

[75] Inventor: Kerry L. Sublette, Tulsa, Okla.

[73] Assignee: Combustion Engineering, Inc., Windsor, Conn.

[21] Appl. No.: 193,712

[22] Filed: May 13, 1988

[51] Int. Cl.$^4$ ............................................. C02F 3/34
[52] U.S. Cl. ................................... 210/611; 210/617; 210/631; 435/264
[58] Field of Search ............... 210/610, 611, 620, 631, 210/903, 616–618; 435/262, 266, 264

[56] References Cited

U.S. PATENT DOCUMENTS

| 4,155,810 | 5/1979 | Kitajima et al. | 210/620 |
| 4,760,027 | 7/1988 | Sublette | 435/266 |

FOREIGN PATENT DOCUMENTS

| 0218958 | 4/1987 | European Pat. Off. | 435/266 |
| 3414556 | 10/1985 | Fed. Rep. of Germany | 210/610 |
| 53-59254 | 5/1978 | Japan | 210/610 |
| 53-90192 | 8/1978 | Japan | 210/611 |
| 61-90790 | 5/1986 | Japan | 210/616 |

Primary Examiner—Tom Wyse
Attorney, Agent, or Firm—Richard H. Berneike

[57] ABSTRACT

A process for oxidizing the sulfide ($H_2S$, $HS^-$, $S^{-2}$) in sour water to convert the sulfide to sulfate by producing a sulfide tolerant strain of *Thiobacillus denitrificans* and then co-immobilizing the *T. denitrificans* and $CaCO_3$ on or within a carrier to form the biofilter. The sour water is contacted with the biofilter in a continuous process.

5 Claims, 2 Drawing Sheets

4,880,542

BIOFILTER FOR THE TREATMENT OF SOUR WATER

BACKGROUND OF THE INVENTION

Soluble sulfides ($H_2S$, $HS^-$, $S^{-2}$) are often found to contaminate water co-produced with petroleum, anaerobic digester effluents and various industrial wastewaters. The source of these sulfides is generally the reduction of sulfates by sulfate reducing bacteria. These bacteria are strict anaerobes which utilize a rather limited number of organic compounds as a source of carbon and energy such as pyruvate, lactate, acetate and ethanol. However, these compounds are end products of the metabolism of fermentive heterotrophs and are readily available in a consortium of bacteria in an anaerobic environment. Therefore, sulfate reducing bacteria are ubiquitous to virtually any anaerobic environment conducive to microbial growth.

The toxicity and corrosive properties of sulfides dictate stringent control of their release into the environment and contact with iron and steel as in tank, pipelines, valves and pumps. The control of sulfide contamination may be approached in two ways. First, sulfide production may be reduced by inhibiting the growth of sulfate reducing bacteria. For example, in the secondary production of petroleum, water used in flooding operations is treated with a biocide to control sulfate reducing bacteria growth in the injection well, reservoir and piping. Since sulfate reducing bacteria are strict anaerobes, aeration of flooding water can also serve to inhibit sulfide production. These measures are of limited effectiveness, however, because sulfate reducing bacteria are sessile bacteria. That is to say, they are generally found attached to a solid surface entrapped with other bacteria in polysaccharide gels produced by "slime-forming" bacteria. Within these gels the sulfate reducing bacteria find themselves in a somewhat protected environment which biocides and oxygen do not effectively penetrate. Of course, biocide treatment is inappropriate in a situation in which the growth of other microorganisms is to be encouraged, such as in an anaerobic digester. In an anaerobic digester, the growth of sulfate reducing bacteria can sometimes be inhibited by fostering competition between the sulfate reducing bacteria and other heterotrophs for the carbon and energy sources favored by the sulfate reducing bacteria. The success of this approach is, however, dependent upon the type of waste being treated.

If sulfide production cannot be prevented, sour water may be treated by a number of physiochemical methods. One of the more common methods is to strip sulfide-laden waters under acidic conditions with steam, flue gas or methane in a packed or plate-type column. In the case of steam or flue gases, the overhead vapors are condensed and the noncondensables (including $H_2S$) are incinerated. In the case of methane, the noncondensables are typically sent to an amine system and the methane recycled. Hydrogen sulfide recovered from the methane stripping gas is generally incinerated. Each of these processes converts a water pollution problem into an air pollution problem in that the combustion of $H_2S$ produces sulfur dioxide, a regulated pollutant.

Sulfides may also be oxidized to less objectionable thiosulfates by air oxidation at 190° F. However, elevated pressures (50–100 psig) are required and the thiosulfates possess considerable chemical and biochemical oxygen demand.

Lastly, small amounts of sulfides can be precipitated with copper (II) or zinc (II) salts. The resulting insoluble sulfides, however, are considered a hazardous waste in that $H_2S$ will be evolved if the precipitants are exposed to acidic conditions.

It is apparent that new technology is needed in the control of $H_2S$ production by sulfate reducing bacteria and the treatment of sulfide-laden waters to address the limitations inherent in conventional methods described above.

*Thiobacillus denitrificans* is a strict autotroph and facultative anaerobe first described in detail by Baalsrud and Baalsrud (Archiv. Mikrobiol. 20, 34 (1954)). Under anaerobic conditions, nitrate may be used as a terminal electron acceptor with reduction to elemental nitrogen. Thiosulfate, elemental sulfur and sulfide may be used as energy sources with oxidation to sulfate; however, sulfide is an inhibitory substrate. It has been demonstrated that *T. denitrificans* may be readily cultured aerobically or anaerobically in batch or continuous reactors on $H_2S$ (g) under sulfide-limiting conditions. Complete removal of $H_2S$ from feed gases was observed with complete oxidation of $H_2S$ to sulfate which accumulated in the culture media. Stable reactor operation was achieved in batch cultures and continuous cultures at reactor loadings as high as 4–5 mmoles $H_2S$ oxidized/hr-g biomass. Maximum $H_2S$ loading of the biomass was estimated at 5.4–7.7 mmoles $H_2S$/hr-g biomass under anaerobic conditions and 15.1–20.9 mmoles $H_2S$/hr-g biomass under aerobic conditions. Recovery from upset conditions has been demonstrated and heterotrophic contamination of *T. denitrificans* cultures has been shown to have no effect on $H_2S$ oxidation.

SUMMARY OF THE INVENTION

The current invention comprises a process by which inorganic sulfides ($H_2S$, $HS^-$ and $S^{-2}$) in water are oxidized to sulfate by supplementing the water with nutrients and contacting said sulfide-laden water with sulfide-tolerant strains of the autotropic bacterium, *T. denitrificans*, co-immobilized with $CaCO_3$. The required nutrients are oxygen or nitrate in the absence of oxygen, inorganic phosphate, a source of reduced nitrogen, magnesium ion, manganese (II) ion and iron (III) ion. The immobilization matrix may be in the form of beads, pellets, plates, tubes, mats, fibers or any other form which facilitates efficient contacting of sour water and the biomass. The biomass may be associated with the immobilization matrix through adsorption, physical entrapment or chemical cross-linking. The $CaCO_3$ must be entrapped in such a way that the salt may contact and react with hydrogen ion resulting as a by-product of the oxidation of sulfide by the bacterium.

DESCRIPTION OF THE PREFERRED EMBODIMENT

Figure 1:
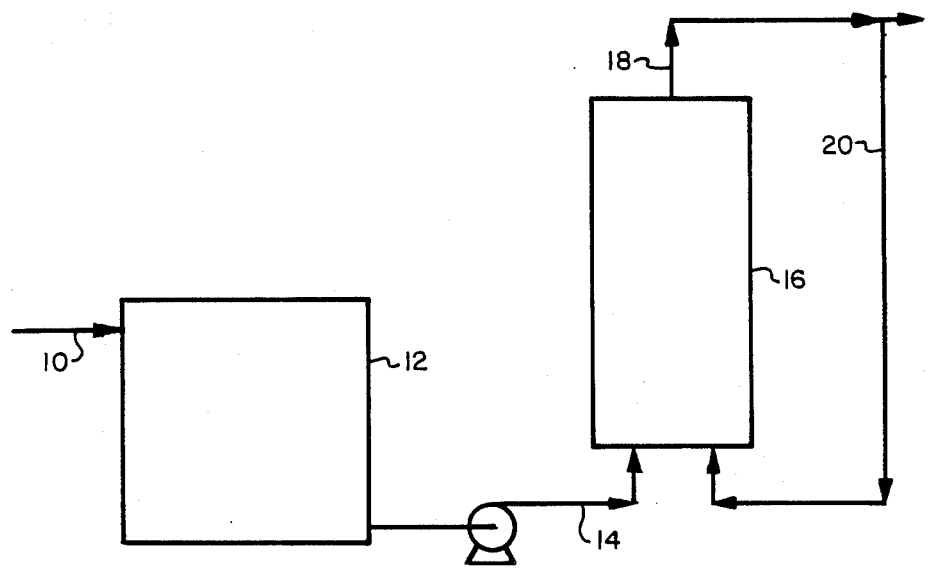
FIG. 1 is a schematic diagram of the system and process of the present invention.

Processes for the removal of $H_2S$ from gases based upon contacting of a sour gas stream with a culture of *T.*

*denitrificans* under sulfide-limiting conditions have been described and claimed in U.S. Patent Application Ser. No. 787,219 filed Oct. 15, 1985, and U.S. patent application Ser. No. 849,646 filed Apr. 9, 1986 U.S. Pat. No. 4,760,027. The stoichiometry of aerobic and anaerobic oxidation of *T. denitrificans* is also described herein and is summarized in Table 1.

In a preferred embodiment of the current invention, a sulfide-tolerant strain of *T. denitrificans*, described hereinafter, is immobilized in the pores of a composite material consisting of an inert support, necessary binders and $CaCO_3$ fashioned into porous beads or pellets in a packed bed or fluidized bed. Alternately, the biomass and $CaCO_3$ may be entrapped in a gel of natural or synthetic polymers maintained by a suitable cross-linking agent. In a fixed bed application, the mechanical properties of the biocatalyst beads, especially compression behavior, are of primary interest.

*trificans* is acid producing. The $CaCO_3$ acts as a buffer neutralizing the acid by-product of sulfide oxidation as shown in the equation below.

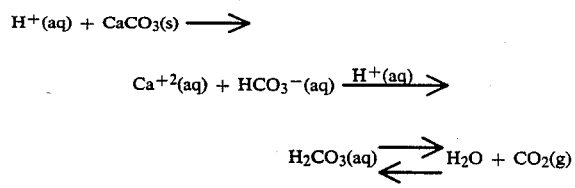

This reaction also produces bicarbonate and $CO_2$ which serves as a carbon source to support the growth of *T. denitrificans* and generates $Ca^{+2}$ internal to the bead which maintains the mechanical stability of the bead. Although reference has been made throughout the use

TABLE 1

| | STOICHIOMETRY OF $H_2S$ OXIDATION BY *THIOBACILLUS DENITRIFICANS* | | | | | | |
|---|---|---|---|---|---|---|---|
| Reactor Type | Electron Acceptor | $NO_3^-/H_2S$ (mole/mole) | $O_2/H_2S$ (mole/mole) | $SO_4^{-2}/H_2S$ (mole/mole) | $NH_4^+/H_2S$ (mole/mole) | $OH^-/H_2S$ (eg/mole) | Biomass/$H_2S$ (g/mole) |
| Batch CSTR | $NO_3^-$ | 1.36 | | 1.04 | 0.12 | 1.60 | 12.1 |
| D = 0.029 $hr^{-1}$ CSTR | $NO_3^-$ | 1.30 | | 1.03 | 0.09 | 1.37 | 9.3 |
| D = 0.058 $hr^{-1}$ CSTR | $NO_3^-$ | 1.19 | | 1.00 | 0.10 | 1.24 | 12.9 |
| Batch CSTR | $O_2$ | | 1.81 | 0.99 | 0.10 | 1.75 | 4.5 |
| D = 0.030 $hr^{-1}$ CSTR | $O_2$ | | | 1.06 | 0.11 | 2.38 | 8.1 |
| D = 0.053 $hr^{-1}$ | $O_2$ | | | 1.04 | 0.12 | 1.77 | 7.9 |

Biocatalyst beads fashioned from inorganic supports, such as diatomaceous earth, exhibit little deformation under forced fluid flow conditions. Gels are subject to deformation under gravity in tall columns and at high fluid flow rates resulting in high pressure drops in the bed. However, in porous biocatalyst beads, internal mass transfer resistances can decrease the effectiveness of the immobilized biomass. Gels, on the other hand, are primarily water; therefore, internal mass transfer resistances are smaller than in the porous biocatalyst bead or pellet and catalyst effectiveness factors are higher.

Each of the immobilization matrices described above has its own advantages and disadvantages. The choice of the possible immobilization matrices for use with the present invention will be dependent upon the precise application. The co-immobilization of a sulfide tolerant strain of *T. denitrificans* and $CaCO_3$ in alginate beads and subsequent anaerobic oxidation of sulfide in sour water will serve to illustrate the current invention.

Alginate is a natural biopolymer which will form a gel in which biopolymer chains are cross-linked with $Ca^{+2}$ ions. Typically, microbial cells may be entrapped in alginate gel beads by blending a suspension of cells with 1.5-3% solution of sodium alginate and adding the resulting mixture dropwise to a 2% solution of $CaCl_2$. When the drops contact the $CaCl_2$ solution, the alginate chains cross-link with $Ca^{+2}$ and the drop hardens into a gel bead. In general, these biocatalyst beads must be utilized in an environment containing sufficient $Ca^{+2}$ ion to prevent $Ca^{+2}$ ions from leaching from the bead and destroying the matrix. This requirement places limitations on the use of these gels in a continuous process.

When $CaCO_3$ is co-immobilized with *T. denitrificans* in alginate beads, the $CaCO_3$ has three functions. First, as noted in Table 1, the oxidation of sulfide by *T. deni-* of $CaCO_3$, any equivalent salt may be used which provides the necessary buffering capacity and is relatively insoluble in water. In addition, if the carrier is a biopolymer such as an alginate gel, the salt must liberate cations which bridge the biopolymer chain and maintain the structural integrity of the carrier.

Figure 2:
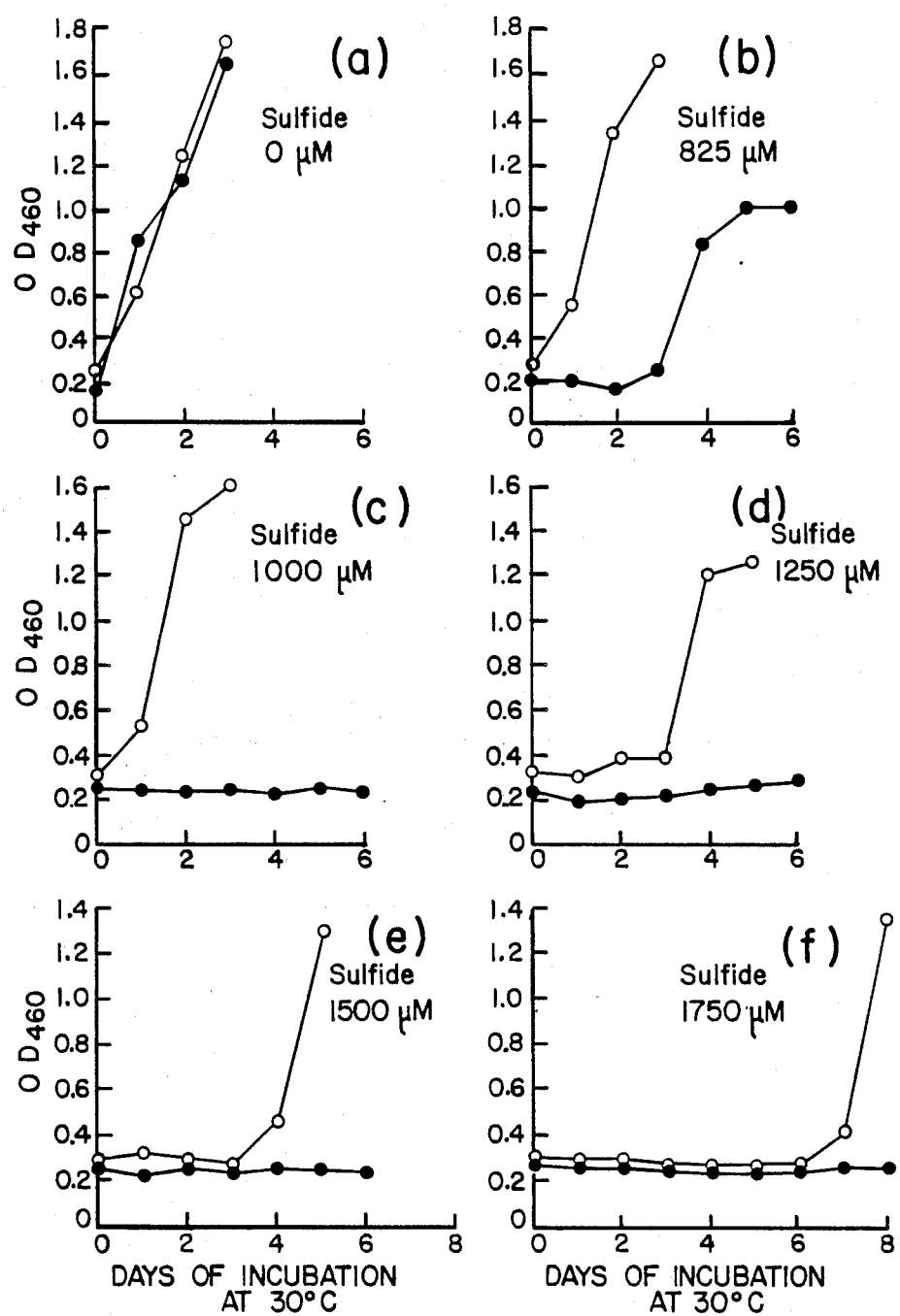
FIG. 2 is a series of graphs (a) to (f) comparing the growth of a sulfide tolerant strain of *T. denitrificans* to the growth of a wild-type strain on thiosulfate in liquid culture at various initial sulfide levels.

Sulfide is an inhibitory substrate with inhibition of growth observed at sulfide concentrations in excess of 100–200 $\mu M$. Total inhibition of growth is observed at about 1000 $\mu M$. Since sulfides are an inhibitory substrate for the growth of *T. denitrificans*, and since the sour waters which would be treated by use of the present invention would most likely have sulfide concentrations that would kill the culture, a sulfide tolerant strain of *T. denitrificans* is employed. A sulfide tolerant strain is obtained by conventional subculturing techniques well known in the art during which spontaneous mutation occurs. A wild-type strain of *T. denitrificans* is first subjected to relatively low levels of sulfide ($Na_2S$) from which will survive those mutants or strains having some low level of sulfide tolerance. The remaining active strains are then repeatedly subcultured in the presence of increasing concentrations of sulfide with growth of the remaining active strains at each step. For purposes of the present invention, strains of *T. denitrificans* tolerant to levels of sulfide up to 1000 $\mu M$ or even higher are desired. The tolerance of a sulfide tolerant strain of *T. denitrificans* as compared to the wild-type is illustrated in FIG. 2 (*a*) to (*f*). These graphs clearly show that the wild type does not grow at sulfide levels of 1000 $\mu M$ or above while the tolerant strain still thrives.

A sulfide tolerant strain of *T. denitrificans* was co-immobilized with $CaCO_3$ in alginate gel beads as follows. This strain of *T. denitrificans* was grown anaerobically in thiosulfate maintenance medium (Table 2) at 30° C. and pH 7.0 in a B. Braun Biostat M fermenter.

TABLE 2

Thiosulfate Maintenance Medium for *Thiobacillus denitrificans*

| Component | Per liter |
|---|---|
| $Na_2HPO_4$ | 1.2 g |
| $KH_2PO_4$ | 1.8 g |
| $MgSO_4.7H_2O$ | 0.4 g |
| $NH_4Cl$ | 0.5 g |
| $CaCl_2$ | 0.03 g |
| $MnSO_4$ | 0.02 g |
| $FeCl_3$ | 0.02 g |
| $NaHCO_3$ | 1.0 g |
| $KNO_3$ | 5.0 g |
| $Na_2S_2O_3$ | 10.0 g |
| *Trace metal solution | 15.0 mL |
| Mineral water | 50.0 mL |

*Described in American Type Culture Collection, Catalog of Strains I, ATCC, Rockville, MD (1982)

The culture was continuously sparged with 30 ml/min. of 5% $CO_2$ in nitrogen to ensure continuous availability of a carbon source. Approximately 36-48 hrs. was required for the culture to reach an optical density at 460 nm of 0.9-1.0. This corresponds to a cell density of approximately $10^9$ cells/ml. When this cell density had been achieved, cells were harvested by centrifugation at 4900×g for 10 min. at 25° C. and resuspended in 100 ml of fresh thiosulfate medium. The concentrated cell suspension was then mixed with an equal volume of 4 wt % sodium alginate (low viscosity, *Macrosystis pyrifera* from Sigma Chemical Co.) and sufficient powdered $CaCO_3$ added to bring the concentration to 30 g/l. The resulting mixture was then pumped through a vertically placed Pasteur pipette (orifice diameter 1.5 mm) at a rate sufficient to produce 50 drops/min. The drops thus formed fell into a 2% $CaCl_2$ which was stirred with a magnetic stirrer. The drops hardened instantly to produce beads approximately 3 mm in diameter.

Gel beads with immobilized *T. denitrificans* and $CaCO_3$ were washed with distilled water and resuspended in fresh thiosulfate maintenance medium in the Biostat M fermenter. The suspension was agitated at 150 rpm and sparged with 30 ml/min. of 5% $CO_2$ in nitrogen. After two days of incubation at 30° C., the thiosulfate in the medium was depleted indicating that the immobilized biomass was active. Microscopic examination of bead material indicated large numbers of gram-negative rods indicative of *T. denitrificans*. At this time, beads were collected by gravity settling and placed in 2% $CaCl_2$ for 10 min. Approximately 20 ml of beads were washed free of $CaCl_2$ and placed in a 17 cm Plexiglass column with an inside diameter of 1.3 cm. Each end of the column was plugged with glass wool. The total height of bead packing was 12.5 cm. A control column was prepared identical in all respects to the test column with the exception that the beads in the control column contained only $CaCO_3$ and no biomass.

Thiosulfate has been shown to be inhibitory to $H_2S$ oxidation by *T. denitrificans*. In order to remove the last traces of thiosulfate from the biocatalyst and control beads, both columns were subjected to an up-flow feed rate of 60 ml/hr of thiosulfate maintenance medium minus thiosulfate at 23° C. for 24 hrs.

At the end of this time, the feed to both columns was changed to maintenance medium minus thiosulfate which was continually sparged with 35 ml/min. of 1% $H_2S$, 5% $CO_2$ with the balance being nitrogen. The feed rate to both columns was 60 ml/hr and each column was operated at 23° C. The effluent from each column was returned to the feed reservoirs. The continuous sparging of the feed reservoirs with 1% $H_2S$ gave a constant total sulfide concentration in the feed of approximately 800 μM or 26 ppm. Recirculation of the feed allowed sulfate to accumulate and be more accurately quantified. A schematic diagram of the system is given in FIG. 1.

After 24 hrs. of operation with sour water feed, the biocatalyst beads in the control column were breaking down badly. Apparently, $Ca^{+2}$ was continually being leached from these beads resulting in solubilization of the alginate. At this time the control column was repacked with glass beads of comparable size to the biocatalyst beads in the test column so as to give the feed approximately the same residence time in the control column as in the test column.

Both columns were operated for 13 days with daily sampling of the feed reservoirs and column effluents. Total sulfide was determined by the methylene blue method. Sulfide was precipitated with zinc acetate and stored as a suspension of ZnS until analysis. Sulfate was determined turbidometrically by precipitation as $BaSO_4$. Nitrate was determined by the cadmium reduction method using gentistic acid in place of N-(1-napthyl)-ethylenediamine in the color development step. Nitrite was determined by the diazotization method using chromatropic acid and sulfanilic acid.

It has been shown that *T. denitrificans* requires 8.3 μg/ml $Fe^{+3}$ for optimum growth. The medium described in Table 1 which was used (without thiosulfate) as the feed contains $FeCl_3$ as a source of iron. However, when the $H_2S$ purge of this medium was begun, a black precipitate of iron and manganese sulfides was obtained as expected. This precipitate was filtered out by the column packings during the first 24-48 hrs of operation. It was a surprising and unexpected result of these experiments to find that the presence of these sulfide precipitates in the column provided a sufficient source of these cations to maintain the viability of the biomass.

No sulfide could be detected in the effluent of the test column (with biomass) either by colorimetric analysis or by odor during the entire course of operation. Correspondingly, a total of 13.2 mmoles of sulfate accumulated in the feed reservoir of the test column as sulfide was oxidized in the column. The cumulative sulfide feed to the column during the course of the experiment was 15.0 mmoles. Apparently, some sulfate precipitated in the beads as $CaSO_4$. Nitrate was utilized during the course of sulfide oxidation as indicated by a decrease in the nitrate concentration in the feed reservoir, the accumulation of nitrite in the feed reservoir, and the appearance of gas bubbles (presumably nitrogen or nitrous oxide) in the test column and the return lines to the feed reservoir. The pH of the column effluent was observed to fall from 6.9 to 6.55 during the course of the experiment. As noted previously, the oxidation of sulfide by *T. denitrificans* is an acid producing process. *T. denitrificans* is typically inhibited by a pH less than 6.6. However, the column was functioning normally when the experiment was terminated and active cells (as indicated by copious growth on thiosulfate agar) were readily recovered from the beads. The pH internal to the beads could have been higher than that of the bulk liquid phase in the column. It can safely be said that the $CaCO_3$ did provided buffering capacity inside the bead. As noted above, control beads without biomass and, therefore, without the internal biologically produced acid fell apart within 24 hrs of the initiation of a continuous feed. However, the biocatalyst beads in the test column maintained structural integrity during the entire course of the experiment indicating internal generation of $Ca^{+2}$.

In contrast to the above description of the present invention, the effluent from the control column with $CaCO_3$ but no biomass contained an average of 200 µM sulfide and smelled strongly of $H_2S$ during the entire course of operation. Apparently, some chemical oxidation of sulfide occurred in the control column and feed reservoir. A total of 6.8 mmoles of sulfate accumulated in the reservoir during the course of the operation. No nitrite could be detected in any samples of the column effluent or feed reservoir.

Referring now to the drawing, the sour water feed 10 is fed to an equalization or surge tak or basin 12. This functions to collect a quantity of feed over a desired period of time in order to avoid heavy surges or loadings of sulfide on the biofilter that might occasionally appear in the feed. The mixed feed from the tank 12 is then pumped through line 14 to the biofilter 16. The treated water is then discharged through line 18 for use or further treatment as may be desired.

The process described above clearly illustrates that viable cells of the autotroph *T. denitrificans* co-immobilized with $CaCO_3$ in alginate beads can be used to remove soluble sulfides from sour water with anaerobic oxidation to sulfate. The $CaCO_3$ provides buffering capacity and generates $Ca^{+2}$ internal to the bead to maintain structural integrity during extended periods of operation. The production of nitrite described above may indicate that the cells were under stress due to excessive sulfide concentrations in the inlet section of the column. Sulfide concentrations in excess of 100–200 µM can result in the incomplete reduction of nitrate by free-cell wild-type *T. denitrificans* under anaerobic conditions, with accumulations of nitrite and nitrous oxide ($N_2O$). Therefore, the accumulation of nitrite in the test column effluent may indicate that for highest removal efficiencies all catalysts beads should "see" a uniform and low concentration of sulfide in the contacting stage. This can be accomplished by partial recycle of the effluent stream to the inlet of the column resulting in greater liquid feed rates but lower inlet sulfide concentration. This is shown in FIG. I by the recycle stream 20.

Although the process of the present invention has been described with reference to an organic matrix, inorganic matrices as described above would produce similar results. In addition, it has been shown that *T. denitrificans* readily oxidize $H_2S$ to sulfate under aerobic conditions with the critical oxygen concentration being about 25 µM. Therefore, oxygen (in concentrations in excess of 25 µM) can be substituted for nitrate in the process with similar results.

I claim:

1. A process for oxidizing the inorganic sulfide in a water stream to form the corresponding sulfate comprising the steps of:
    (a) providing a sulfide tolerant strain of *T. denitrificans* tolerant of levels of sulfide in excess of 1000 µM;
    (b) immobilizing said strain together with calcium carbonate on or within a carrier;
    (c) providing nutrient for said strain within said water stream including iron ions which precipitate when contacted with sulfides; and
    (d) contacting said water containing said sulfides and nutrient with said immobilized strain and calcium carbonate in a packed or fluidized bed reactor whereby said strain oxidizes said sulfide to sulfate and whereby said strain derives iron nutrient from said precipitated iron.

2. A process as recited in claim 1 wherein said carrier is porous.

3. A process as recited in claim 1 wherein said carrier is an alginate gel and wherein the calcium ions of said calcium carbonate cross-link said alginate gel.

4. A process as recited in claim 1 wherein said process is carried out under anaerobic conditions and wherein said nutrient includes a nitrite as the terminal electron acceptor.

5. A process as recited in claim 1 wherein a portion of the contacted water which has been treated to remove sulfide is recycled to said contacting step (d) to dilute the sulfude concentration.

* * * * *